United States Patent [19]

Buerstinghaus et al.

[11] Patent Number: 4,775,666
[45] Date of Patent: Oct. 4, 1988

[54] BISTHIOLPHOSPHATE, THEIR USE FOR COMBATTING PESTS

[75] Inventors: Rainer Buerstinghaus, Heidelberg; Karl Kiehs, Lampertheim; Heinrich Adolphi, Limburgerhof; Volker Harries, Frankenthal, all of Fed. Rep. of Germany

[73] Assignee: BASF Aktiengesellschaft, Ludwigshafen, Fed. Rep. of Germany

[21] Appl. No.: 922,997

[22] Filed: Oct. 24, 1986

[30] Foreign Application Priority Data

Oct. 25, 1985 [DE] Fed. Rep. of Germany ....... 3537999

[51] Int. Cl.$^4$ ...................... A01N 57/02; C07F 9/165
[52] U.S. Cl. ..................................... 514/119; 558/170
[58] Field of Search ..................... 558/170; 514/119

[56] References Cited

U.S. PATENT DOCUMENTS

| 2,996,531 | 8/1961 | Young | 558/170 |
| 3,806,560 | 4/1974 | Kishino et al. | 558/170 |
| 3,969,439 | 7/1976 | Urbach et al. | 558/170 |

FOREIGN PATENT DOCUMENTS 814587 6/1959 United Kingdom .

Primary Examiner—Anton H. Sutto
Attorney, Agent, or Firm—Keil & Weinkauf

[57] ABSTRACT

Bisthiolphosphates of the formula

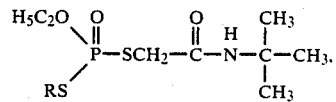

where R is alkyl, and pesticides containing these compounds.

8 Claims, No Drawings

BISTHIOLPHOSPHATE, THEIR USE FOR COMBATTING PESTS

The present invention relates to novel bisthiolphosphates, a process for their manufacture, pesticides containing these bisthiolphosphates as active ingredients, and a process for combatting pests with these active ingredients.

Active ingredients from the group of phosphorylated acetamides suitable for combatting pests have been disclosed for example in Belgian Pat. No. 562,144. They are suitable as insecticides and acaricides. However, their action, especially at low concentrations,is not always completely satisfactory.

We have now found that bisthiolphosphates of the formula

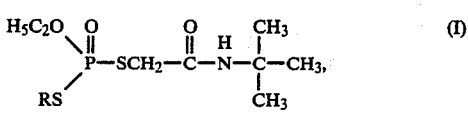

where R is branched or straight-chain alkyl of 3 or 4 carbon atoms, combat pests from the class of insects—particularly nematodes—more effectively than prior art active ingredients of a similar structure.

Examples of alkyl radicals for R are n-propyl, isopropyl, isobutyl, sec-butyl and tert-butyl.

The novel compounds are produced by reacting the prior art halo-N-tert-butylacetamide of the formula

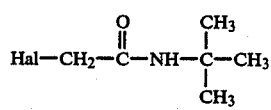

with a salt of an appropriate dithiophosphoric acid derivative of the formula

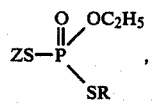

where Z is an alkali metal ion, one equivalent of an alkaline earth metal ion or an ammonium ion which is unsubstituted or substituted by alkyl.

Halogen in formula II is especially chlorine or bromine. In formula III, Z is preferably sodium, potassium, ammonium or methylated ammonium.

The reaction is carried out in the manner usual for reacting organic halogen compounds with alkali metal salts, e.g., below 150° C. in a solvent or diluent. If a non-aqueous solvent is used, it may be expedient to add a catalytic amount of potassium iodide or a complexing agent, e.g., a crown ether, to increase the reactivity.

The novel compounds are obtained from the reaction mixture in the usual manner, e.g., by adding water, separating the phases, followed by distillation and/or column chromatography.

Some of the novel compounds of the formula I are obtained as colorless or slightly brownish colored oils, which are freed from the last volatile constituents by prolonged heating under reduced pressure at moderately elevated temperature ("incipient distillation"), and thus purified.

The preparation of the compounds according to the invention is illustrated by the following example.

PREPARATION EXAMPLE 1

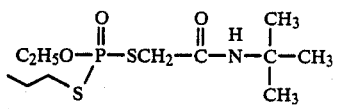

A mixture of 1,100 g of potassium-O-ethyl-S-n-propyldithiophosphate, 2,500 ml of acetonitrile, 627 g of N-tert-butyl-2-chloroacetamide and 1 g of 18-crown-6 is heated at 80° C. for 14 hours. After the mixture has cooled, the solvent is stripped off in a rotary evaporator, the residue is taken up in methyl tert-butyl ether and washed 5 times with 5% strength aqueous sodium hydroxide solution and 5 times with water. After drying over sodium sulfate, the solvent is removed under reduced pressure, and the residue subjected to incipient distillation at 0.01 mbar and 60° C. There is obtained 862.5 g of O-ethyl-S-n-propyl-S-(N-tert-butylacetamido)-dithiophosphate as a pale brown oil. Yield: 65% of theory.

|  | $C_{11}H_{24}NO_3PS_2$ (313) | | |
|---|---|---|---|
|  | C | H | S |
| Calc.: | 42.2 | 7.8 | 20.4 |
| Found: | 42.4 | 7.8 | 20.3 |

Infrared absorptions from the "fingerprint" range (cm$^{-1}$): 1549, 1244, 1226, 1016, 955, 598.

| Ex. no. | R | Infrared absorptions (cm$^{-1}$) |
|---|---|---|
| 2 | isopropyl | 1546, 1245, 1225, 955 |
| 3 | isobutyl | 1547, 1390, 1355, 1223, 1018, 950 |
| 4 | sec-butyl | 1545, 1390, 1360, 1220, 1020, 950 |
| 5 | tert-butyl |  |

The bisthiolphosphates of the formula I are suitable for effectively combatting pests from the class of insects, arachnids and nematodes. They may be used for crop protection, and in the hygiene, stores protection and veterinary sector as pesticides.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinra nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis flammaea, Earias insulana, Plusia gamma, Alabama argillacea, Lymantria dispar, Lymantria monacha, Pieris brassicae,* and *Aporia crataegi;*

Examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris,*

*Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otirorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;*

Examples from the Diptera order are *Lycoria pectoralis, Mayetiola destructor, Dasyneura brassicae, Contarinia tritici, Haplodiplosis equestris, Tipula paludosa, Tipulaoleracea, Dacus cucurbitae, Dacus oleae, Ceratitis capitata, Rhacoleti cerasi, Rhaqoletis pomonella, Anastrepha ludens, Oscinella frit, Phorbiacoarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina. morsitans, Oestrus ovis, Chrysomya macellaria, Chrysomya hominivorax, Lucilia cuprina, Lucilia sericata,* and *Hypoderma lineata;*

Examples from the Hymenoptera order are *Athalia rosae, Hoplocampa minuta, Monomorium pharaonis, Solenopsis geminata,* and *Atta sexdens;*

Examples from the Heteroptera order are *Nezara viridula, Eurygaster integriceps, Blissus leucopterus, Dysdercus cingulatus, Dydercus intermedius, Piesma quadrata,* and *Lygus pratesis;*

Examples from the Homoptera order are *Perkinsiella saccharicida, Nilaparvata lugens, Empoasca fabae, Psylla mali, Psvlla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis* and *Viteus vitifolii;*

Examples from the Isoptera order are *Reticulitermes lucifugus, Calotermes flavicollis, Leucotermes flavipes,* and *Termes natalensis;*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus longatus,* and *Trichodorus primitivus.*

The active ingredients may be applied as such, in the form of formulations or application forms prepared therefrom, e.g., as directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 4 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 2 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 3 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably from 0.5 to 90, wt % of active ingredient.

The concentration of active ingredient in the finished preparations may vary over a wide range, but is usually from 0.0001 to 10, and preferably from 0.01 to 1%.

The bisthiolphosphates of the formula I combat pests from the class of insects and particularly nematodes more effectively than prior art compounds of similar structure.

The following compound (A) disclosed in Belgian Pat. No. 562,144

$$\begin{array}{c} CH_3-O \\ \phantom{CH_3-O}\diagdown \underset{\|}{P}-S-CH_2-\underset{\|}{C}-N \diagup\diagdown \\ CH_3-O \diagup \phantom{\underset{\|}{P}-S-CH_2-\underset{\|}{C}-N} \diagdown\diagup \end{array} \quad (A)$$

was used for comparison purposes.

Compounds nos. 1, 2 and 4 selected by way of example have a far better contact action on houseflies (*Musca domestica*) than the comparative agent.

Further, compounds nos. 2 and 4 for example have a far better contact action on granary weevils (*Sitophilus granarius*) than the comparative agent.

The contact action on cockroaches (Blatta orientalis) of compounds nos. 1, 2, 3 and 4 is better than that of the comparative agent.

For instance compounds nos. 1, 2 and 4 have, in a breading experiment, a better action on larvae of the flour moth (*Ephestia kuehniella*) than compound A.

The contact action and effect of ingested food on caterpillars of the diamondback moth (*Plutella maculipennis*) is for example better with compounds nos. 1, 2 and 4 than with the prior art compound.

Compounds nos. 2, 3 and 4 selected by way of example exhibit favorable properties when ticks (*Ornithodorus moubata*) are contacted with them.

The active ingredients may also be successfully used in the ultra-low-volume (ULV) method, in which it is also possible to apply formulations containing more than 95 wt % of active ingredient, or even the active ingredient without additives.

When the active ingredients are used in the open, the application rate is from 0.2 to 10, and preferably from 0.5 to 2.0 kg/ha.

Oils of various types, herbicides, fungicides, other pesticides, and bactericides can be added to the active ingredients, if necessary even directly before use (tank mix). These agents can be mixed with the agents according to the invention in a weight ratio of from 1:10 to 10:1.

We claim:

1. A bisthiolphosphate of the formula $$\begin{array}{c} H_5C_2O \\ \phantom{H_5C_2O}\diagdown \underset{\|}{P}-SCH_2-\underset{\|}{C}-\underset{H}{N}-\underset{CH_3}{\underset{|}{C}}-CH_3, \\ RS \diagup \phantom{\underset{\|}{P}-SCH_2-\underset{\|}{C}-\underset{H}{N}-\underset{CH_3}{C}}CH_3 \end{array} \quad (I)$$

where R is branched or straight-chain alkyl of 3 or 4 carbon atoms.

2. A process for combatting pests, wherein an effective amount of a compound of the formula I as set forth in claim 1 is allowed to act on the pests or their habitat.

3. A pesticide containing a solid or liquid carrier and an effective amount of at least one compound of the formula I as set forth in claim 1.

4. A compound of the formula I as defined in claim 1, wherein R is n-propyl.

5. A compound of the formula I as defined in claim 1, wherein R is isopropyl.

6. A compound of the formula I as defined in claim 1, wherein R is isobutyl.

7. A compound of the formula I as defined in claim 1, wherein R is sec.-butyl.

8. A compound of the formula I as defined in claim 1, wherein R is tert.-butyl.

* * * * *